United States Patent
Lithgow et al.

(10) Patent No.: US 6,918,390 B2
(45) Date of Patent: *Jul. 19, 2005

(54) FOREHEAD SUPPORT FOR FACIAL MASK

(75) Inventors: Perry D. Lithgow, Glenwood (AU); Robert E. Styles, Glenhaven (AU); Zdzislaw A. Ziolkowski, Earlwood (AU); Philip R. Kwok, Chatswood (AU)

(73) Assignee: ResMed Limited, North Ryde (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/685,001

(22) Filed: Oct. 15, 2003

(65) Prior Publication Data

US 2004/0079375 A1 Apr. 29, 2004

Related U.S. Application Data

(63) Continuation of application No. 09/935,778, filed on Aug. 24, 2001, now Pat. No. 6,679,261.
(60) Provisional application No. 60/227,472, filed on Aug. 24, 2000.

(51) Int. Cl.[7] .............................................. A62B 18/08
(52) U.S. Cl. ........................ 128/206.27; 128/205.25; 128/206.21; 128/207.13; 128/207.17
(58) Field of Search ................. 128/207.11, 206.27, 128/207.17, 205.25, 206.12, 206.13, 206.21, 207.18, 204.11, 207.13

(56) References Cited

U.S. PATENT DOCUMENTS

| | | | | |
|---|---|---|---|---|
| 6,119,693 A | * | 9/2000 | Kwok et al. | ............ 128/207.11 |
| 6,463,931 B1 | | 10/2002 | Kwok et al. | |
| 6,532,961 B1 | | 3/2003 | Kwok et al. | |
| 6,557,556 B2 | | 5/2003 | Kwok et al. | |
| 6,679,261 B2 | * | 1/2004 | Lithgow et al. | ....... 128/207.11 |

FOREIGN PATENT DOCUMENTS

| | | |
|---|---|---|
| WO | WO 00/78384 | 2/2000 |
| WO | WO 00/57942 | 10/2000 |

OTHER PUBLICATIONS

Photograph of "Weinmann Mask" known prior to 1998.

* cited by examiner

*Primary Examiner*—Henry Bennett
*Assistant Examiner*—Mital Patel
(74) *Attorney, Agent, or Firm*—Nixon & Vanderhye P.C.

(57) ABSTRACT

The present invention discloses an adjustable forehead support for a nasal or full-face mask wherein the forehead support may be adjusted for the different shapes and sizes of a facial profile. The forehead support utilizes a dual-arm system that adjusts the position of the forehead support vis-á-vis the mask and/or airflow tube. The angle of the mask to the face may be adjusted with the present invention.

28 Claims, 9 Drawing Sheets

FOREHEAD SUPPORT FOR FACIAL MASK

This application is a continuation of application Ser. No. 09/935,778, filed Aug. 24, 2001, now U.S. Pat. No. 6,679,261, which claims the benefit of Provisional application Ser. No. 60/227,472, filed Aug. 24, 2000, incorporated herein by reference in its entirety.

BACKGROUND OF THE INVENTION

1. Field of the Invention

The present invention generally relates to an improved comfort device to be used with a nasal mask. In particular, the device is useful in combination with masks which are used for the treatment of respiratory conditions and assisted respiration. The invention assists in fitting the mask to the face as well.

2. General Background

Nasal masks are commonly used in the treatment of respiratory conditions and sleep disorders by delivering a flow of breathable gas to a patient to either assist the patient in respiration or to provide a therapeutic form of gas to the patient to treat sleep disorders such as obstructive sleep apnea. These nasal masks typically receive a gas through a supply line which delivers gas into a chamber formed by walls of the mask. The mask is generally a semi-rigid mask which has a face portion which covers at least the wearer's nostrils. Additionally, the mask may be a full face mask. The mask is normally secured to the wearer's head by straps. The straps are adjusted to pull the mask against the face with sufficient force to achieve a gas tight seal between the mask and the wearer's face. Gas is thus delivered to the mask and the wearer's nasal passages and/or mouth.

One of the problems that arises with the use of the mask is that in order for the straps to be tight, the mask is compressed against the wearer's face and may push unduly hard on the wearer's nose. Additionally, the mask may move around on the wearer's face. Thus, there has been provided a forehead support, which provides a support mechanism between the mask and the forehead. This forehead support prevents both the mask from pushing too strongly against the wearer's nose and/or facial region as well as minimize movement of the mask with the addition of a contact point between the mask and the wearer's head as well as minimize uncomfortable pressure points of the mask. Additionally, the forehead support may prevent the airflow tube from contacting the wearer's forehead or face.

FIG. 1 shows a general perspective view of a related art forehead support 10. The forehead rest or support 10 is attached to an airflow tube 12 extending from the mask 14. The mask 14 and forehead support 10 are shown with headgear 16 which secures the mask 14 to the head of a patient. As can be seen in FIG. 1, the headgear 16 loops through the forehead support 10 at loops 18 and 20. This pulls the forehead support 10 against the forehead, thus creating a snugly fitted mask 14 and also provides a stabilizing member for the mask 14.

FIG. 2 discloses the construction of the related art forehead support 10. The forehead support 10 has pads 24 and 26, a back side of which can be seen in greater detail in FIG. 10. These pads 24 and 26 are the actual contact points of the forehead support 10 to the forehead. The support pads 24 and 26 are mounted to the bridge 32. Arms 34 and 36 are secured to bridge 32 by an adjustable locking mechanism which is better illustrated in the figures below. The bridge 32 provides three purposes to the forehead support 10. First, it acts as a securing means for pads 24 and 26. Second, it has loops 18 and 20 which receive the optional headgear 16 shown in FIG. 1. Finally, it receives arms 34 and 36, which may be adjusted, as described below. The bridge 32 and arms 34 and 36 operate in a cantilever fashion and are made of a polymeric material, which may be easily molded. Additionally, arms 34 and 36 join together to create an annular space 38 to receive airflow tube 12 which is connected to a flow generator to generate breathable air or some type of therapeutic gas. Arms 34 and 36 create an operational hinge. The tube 12 is an axis of this hinge.

FIG. 3 is an exploded view of FIG. 2 and shows the forehead support 10 in greater detail. Bridge engaging pins 56, 58, 60 and 62 are shown in FIG. 3. As will be more apparent in the figures below, these engaging pins provide for the adjustability of the forehead support 10. Bridge 32 includes slots 76, 78, 82, 84, 86, 88 and 90 (see FIG. 9) and a mirror set of slots on the upper portion of bridge 32 (not visible in FIG. 9) for selectively receiving pins 56, 58, 60 and 62. These slots open to the forehead side of the bridge. Additionally, there is a space or recess at arms 34 and 36 shown on arm 34 as 64. The purpose of this space 64 is so that the user may compress arm 34 and thus press pins 56 and 58 together by pressing on surfaces 66 and 68. The purpose of the compression is to decrease the distance between pins 56 and 58 such that they may be selectively inserted and locked into the desired pair of slots on bridge 32. The length of the pins 56 and 58 is such that even when the pins are pressed together, they do not clear the slots in the bridge sufficiently to allow the arms to be disassembled from the bridge without further action.

FIG. 4 is a side view of the mask 14 and forehead support 10. The mask is shown as 14 with a dotted line showing the nose of a wearer 70 and the dotted line showing the forehead 72 of the wearer. Pad 26 is shown compressed by the forehead of the individual wearing the mask.

FIG. 5 is a top view of the forehead support 10 taken along lines 5 of FIG. 4. Also, the mask 14 is not shown in FIG. 5. This figure illustrates the forehead support 10 in a position wherein the forehead support is in the closest position to the tube 12 (shown as merely a space in FIGS. 5–6). The bridge 32 is shown essentially in contact with tube 12. The pins 56, 58, 60 and 62 are shown in their furthest position from the center of the bridge 32, engaging slot pairs 88 and 90. This position may be utilized by someone with a large, protruding or bulbous forehead, or a high nasal bridge, or someone who prefers the airflow tube to be snug against their forehead. FIG. 6 shows the same forehead support in the next position, wherein the bridge 32 is moved away from tube 12 such that there is a gap 74 between bridge 32 and tube 12. Here, pins 56, 58, 60 and 62 engage slot pairs 76 and 86. As is visible from the figure, the forehead support 10 is now moved away from tube 12, and is positioned differently than in FIG. 5. This may be configured to fit someone with a less protruding forehead, or someone who wants the flexible tube further from their head than is possible in FIG. 5. FIGS. 7 and 8 show the third and fourth position for the forehead support.

The related art arm 34 is shown in greater detail in FIGS. 11–13. As can be seen in the top view of the arm 34 shown in FIG. 11, the arm 34 includes a semicircular portion 100, on an interior of which the annular space 38 is situated. An extending portion 102 extends from the semicircular portion 100. Surfaces 66 and 68, space 64 and engaging pins 56 and 58 are positioned on the extending portion 102. Each surface 66 and 68 includes a generally oval depression 106 and 108, respectively, positioned near the pins 56 and 58. These oval depressions 106 and 108 can be felt by the wearer of the mask and assist the wearer in properly positioning his or her fingers near the pins 56 and 58 when it is desired to adjust the forehead support. This is especially important when the mask and forehead support are positioned on the wearer's head because at such time, the wearer cannot easily see where to place his or her fingers to adjust the forehead support. The oval depressions not only assist the wearer in properly positioning his or her fingers for adjusting the support, by virtue of the fingers engaging the depressions, the depressions also help maintain the fingers in the appropriate position.

FIG. 12 is a side view of the arm shown in FIG. 11. As can be seen there, the semicircular portion 100 only extends upward to half of the height of the arm 34. Because of this, the arm 34 is reversible, i.e., it can be flipped over, and then can be used as arm 36. Thus, only one arm design need be molded and this can be used as both arm 34 and arm 36, depending on its orientation. Extending portion 102 includes two horizontal flanges 110 and 112 connected by an intermediate web 114. The two horizontal flanges are thicker in the horizontal direction and thinner in the vertical direction than web 114. The space 64 is positioned on web 114. The force required to press the pins 56 and 58 together is a function of the amount of material of the extending portion 102 on either side of the space 64 in the vertical direction, the length space 64 extends along portion 102 (i.e., the length of each cantilever arm on either side of space 64) and the type of material from which the arm 34 is constructed. These arms have been constructed of a polycarbonate, specifically, Makrolon 2458 manufactured by Bayer.

FIG. 13 shows a cross-section of the arm 34 along line 13—13 in FIG. 12. The comparative thicknesses of the flange 112 and the web 114 in the horizontal direction can best be seen here. The hatched portion of the arm 34 is the portion of the web 114 beyond the extended length of the space 64.

It has been found that while the related art forehead support performs correctly if operated according to the instructions, an improvement can be made to reduce the risk of breakage when the forehead support is operated in a manner contrary to instructions.

Further, because depressions 106 and 108 are relatively narrow, an improvement can be made to allow the user to positively and firmly position his or her fingers to press the pins 56 and 58 together. Finally, because there is a relatively large amount of material contact between an interior of semicircular portion 100 and an exterior of airflow tube 12, this can result in a relatively large amount of friction between the arm 34 and the tube 12, thereby requiring additional force to pivot the arm 34 around the tube 12 for adjustment purposes.

SUMMARY OF THE INVENTION

The present invention is directed to an improved version of the type of forehead support discussed above. In particular, the present invention utilizes improved arms extending from the mask or gas supply line for adjustably engaging the bridge for allowing positioning of the mask on the face. First, extending portions of the arms are redesigned to compress more easily than the extending portions of the related art arms discussed above while at the same time maintaining the strength necessary for adequately supporting the airflow tube. Thus, the engaging pins may more easily be compressed together to allow for adjustment of the arms with respect to the bridge.

Furthermore, the extending portions of the arms are provided with locking portions that maintain alignment of the pins with respect to one another as they are being compressed to prevent lateral deflection of the pins, unintended stress loading on the arms and to allow easier engagement of the pins with the slots upon release of the extending portions.

Finally, arc portions of the arms that come into contact with the airflow tube 12 are undercut and radiused to prevent sticking or binding of the arms as they are pivoted about the airflow tube during adjustment of the forehead support, as compared to the related arm embodiment. Thus, the arms more easily pivot about the airflow tube during adjustment of the forehead support.

These improvements make it easier to adjust the forehead support, as well as make it easier to disassemble the arms from the bridge to allow thorough cleaning of the bridge and other support components.

DETAILED DESCRIPTION OF THE PREFERRED EMBODIMENT

Figure 14:
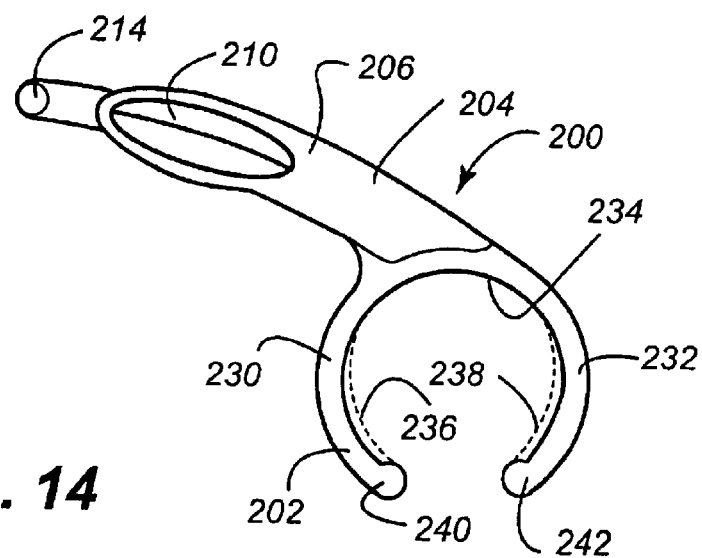
FIG. 14 is a top view of an improved arm for use in the forehead support of FIG. 2.

FIG. 14 shows a top view of an improved embodiment of an arm for use with the present invention. Arm 200 includes a semicircular portion 202 and an extending portion 204 attached thereto. Semicircular portion 202 includes two arc portions 230 and 232 and an inner bore 234. The two arc portions 230 and 232 are both recessed or undercut near their ends, as shown by the phantom lines 236 and 238. Thus, the inner bore 234 is not perfectly circular in shape near the ends of arc portions 230 and 232. Ends 240 and 242 of the arc portions 230 and 232, respectively, are well radiused to prevent binding of the arm on the airflow tube during pivoting.

Figure 12:
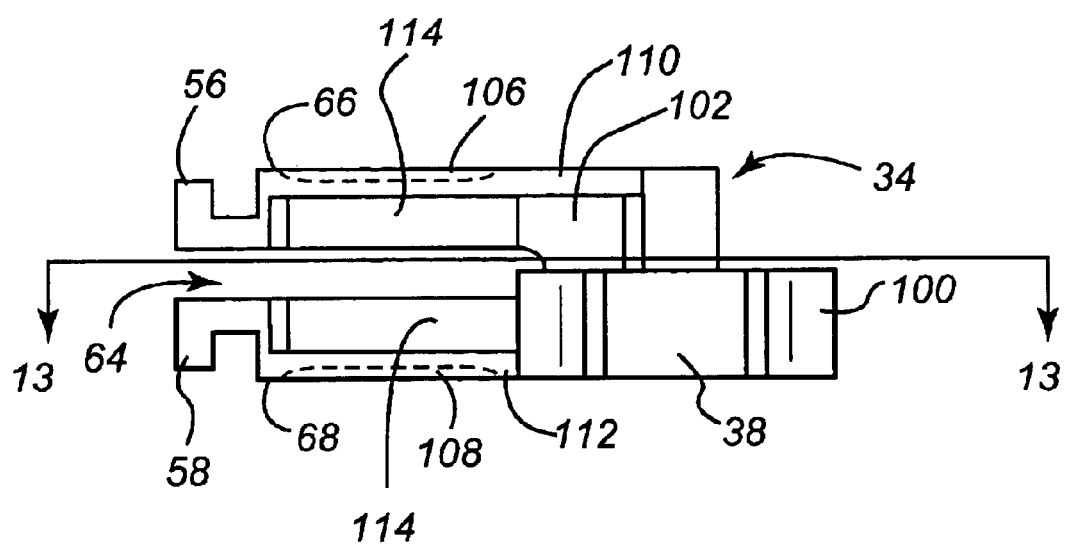
FIG. 12 is a side view of the arm of FIG. 11.
Figure 19:
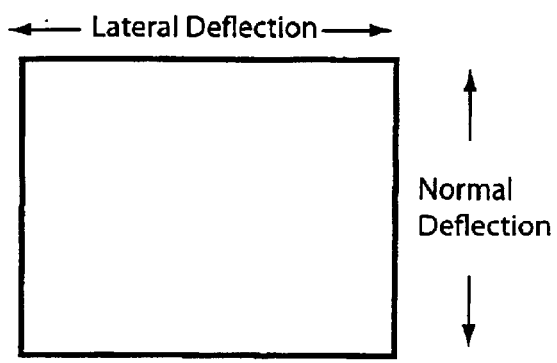
FIG. 19 is a partial section view of the arm of FIG. 15 along section line 19—19.
Figure 20:
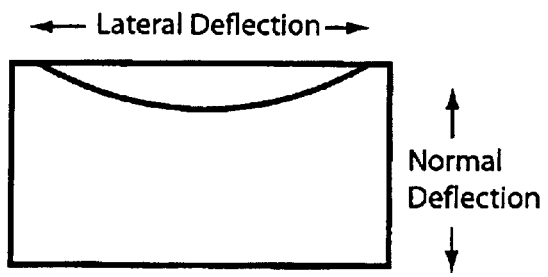
FIG. 20 is a partial section view of the arm of FIG. 15 along section line 19—19.

Extending portion 204 includes two flange portions 206 and 208 on which generally oval depressions 210 and 212 are respectively positioned. Bridge engagement pins 214 and 216 are positioned at far ends of flange portions 206 and 208, respectively, and project, respectively, upwardly and downwardly from the arm 200. A space 218 separates the flange portions 206 and 208 and in this embodiment, it can be seen that there is no vertical web between the respective flange portions and the space 218. Also, it can be seen that the space 218 extends along a greater portion of arm 200 than does the embodiment shown in FIG. 12. Thus, the cantilever arm portions of the arm of FIG. 14 are longer than the cantilever arm portions of the arm of FIG. 2. Further, the cantilever arm portions of the arm of FIG. 14 are tapered along their length, such that the thickness of these portions is less near the pins than the semicircular portion 202. Compare the thicker section of the arm of FIG. 15 shown in FIG. 19 with the thinner section of the arm taken nearer the pin 214 shown in FIG. 20.

Figure 1:
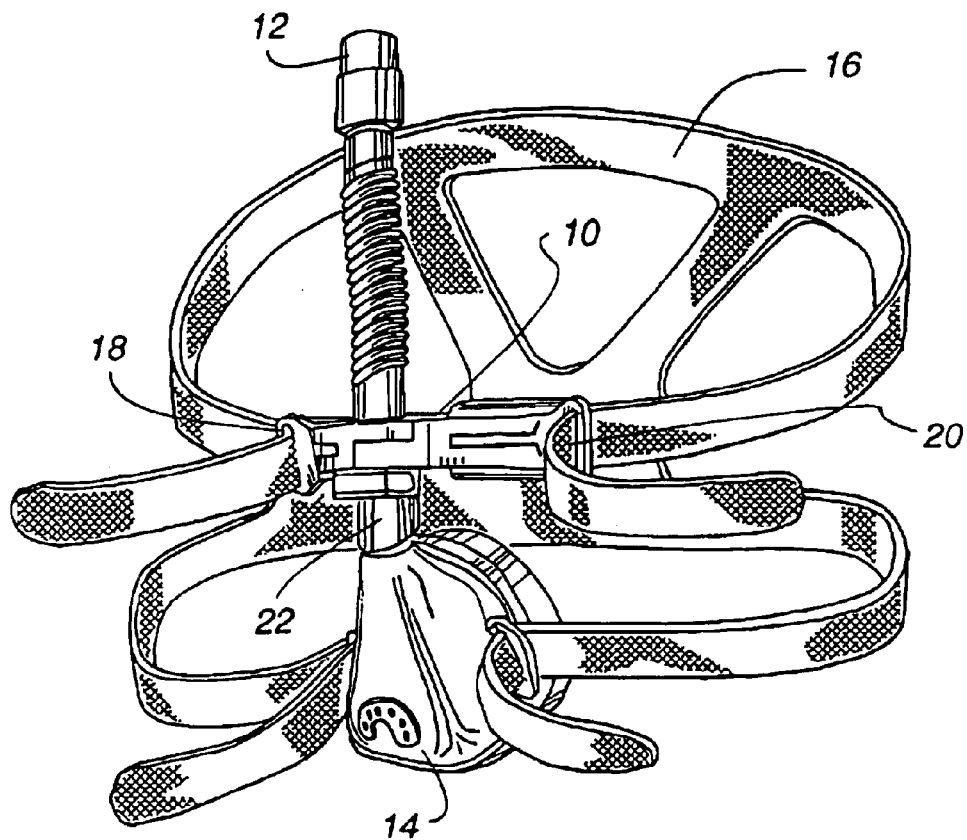
FIG. 1 is a perspective view of a related art forehead support attached to a mask, headgear and a gas supply tube.
Figure 2:
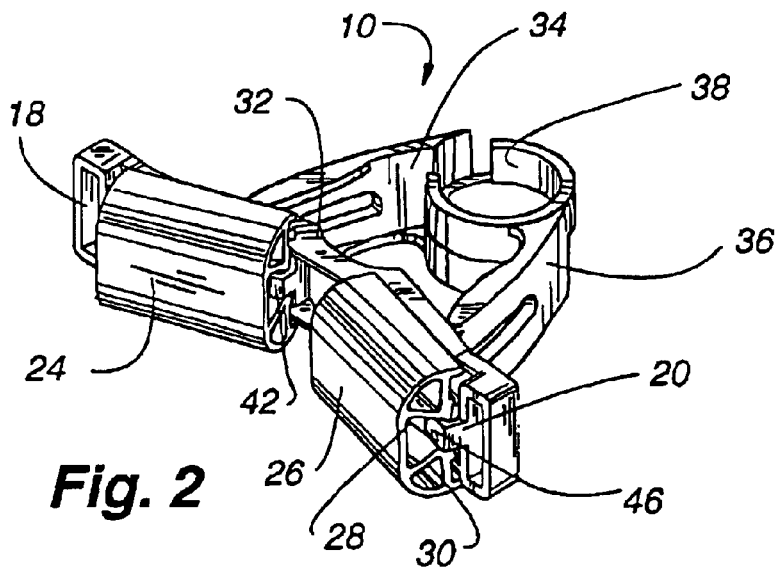
FIG. 2 is a perspective view of the forehead support of FIG. 1 removed from the mask and gas line.
Figure 3:
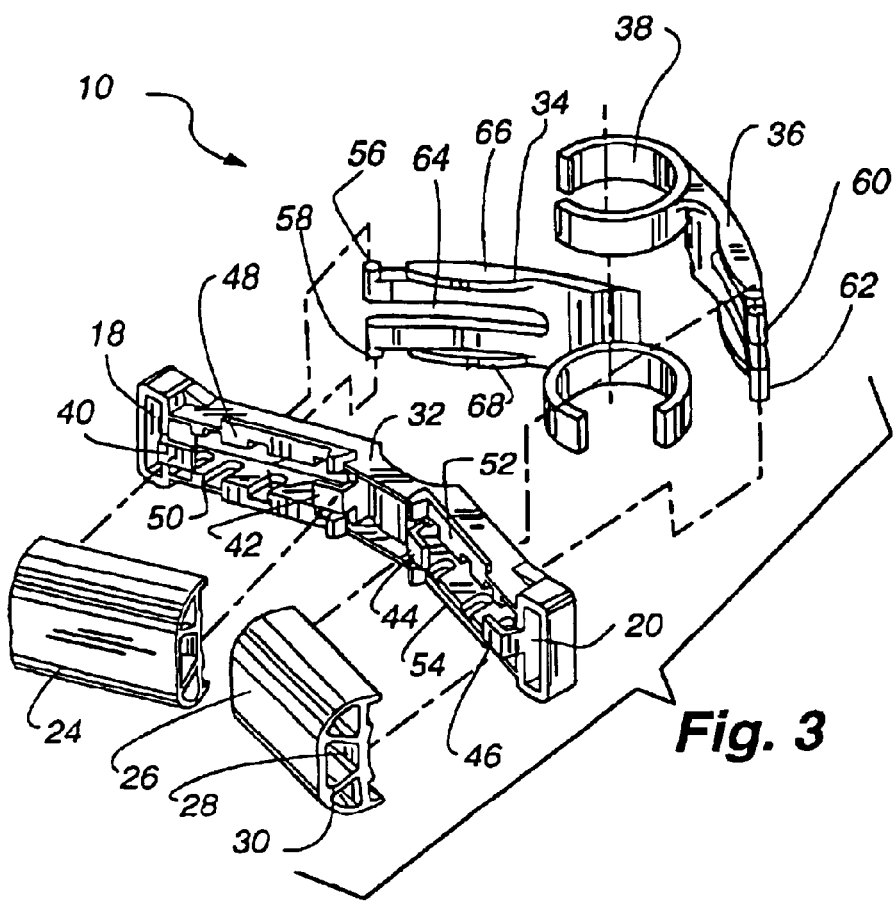
FIG. 3 is an exploded view of the forehead support of FIG. 1.
Figure 4:
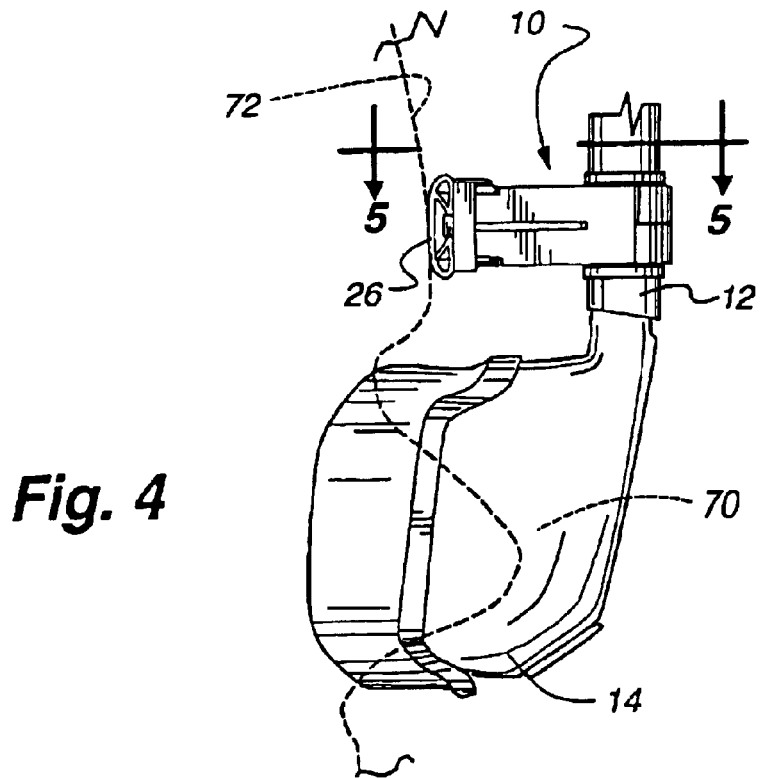
FIG. 4 is a side view of the forehead support of FIG. 1 secured to a mask.
Figure 5:
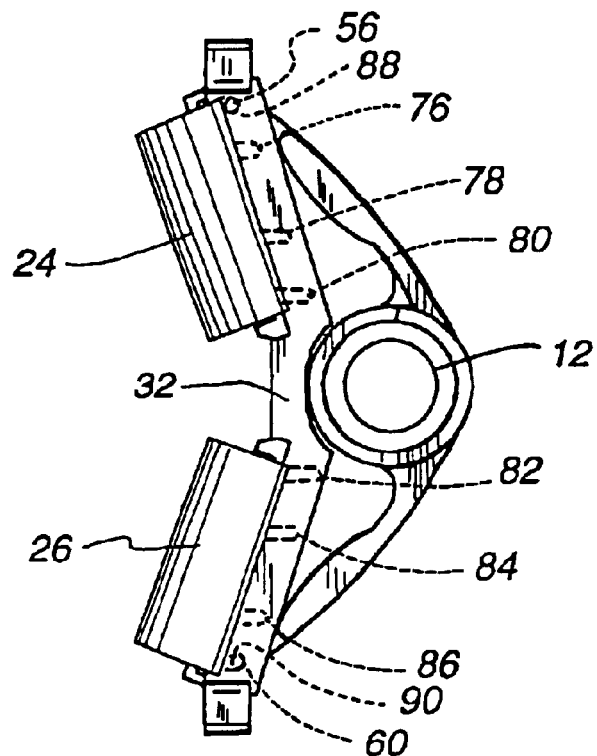
FIG. 5 is a top view of the forehead support of FIG. 1 in a first position.
Figure 6:
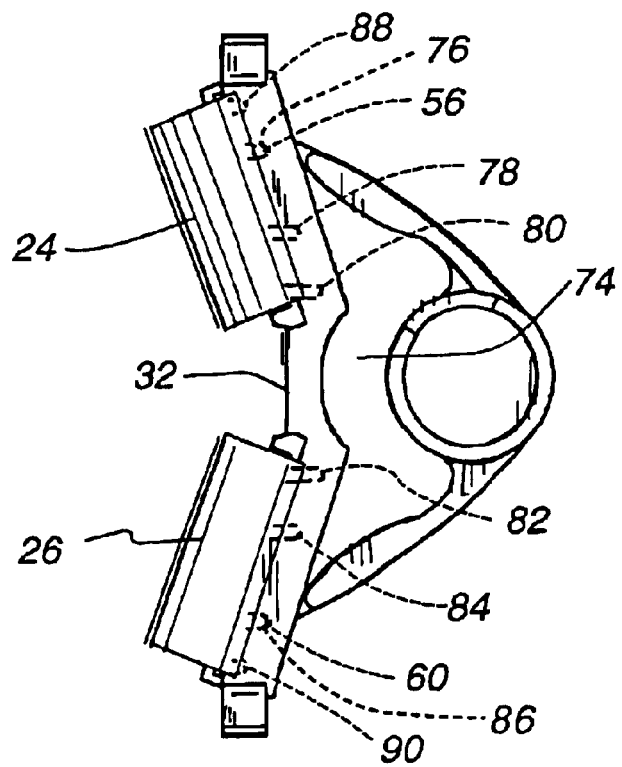
FIG. 6 is a top view of the forehead support of FIG. 1 in a second position.
Figure 7:
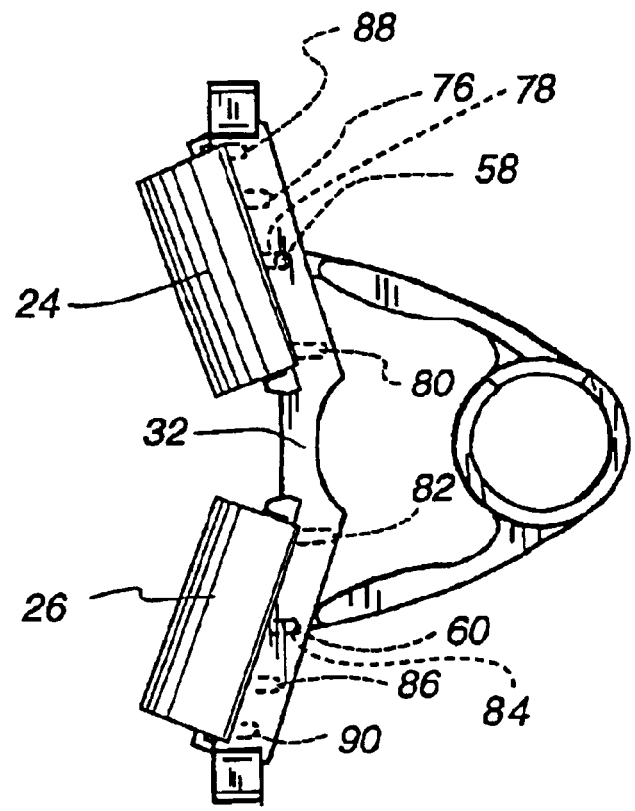
FIG. 7 is a top view of the forehead support of FIG. 1 in a third position.
Figure 8:
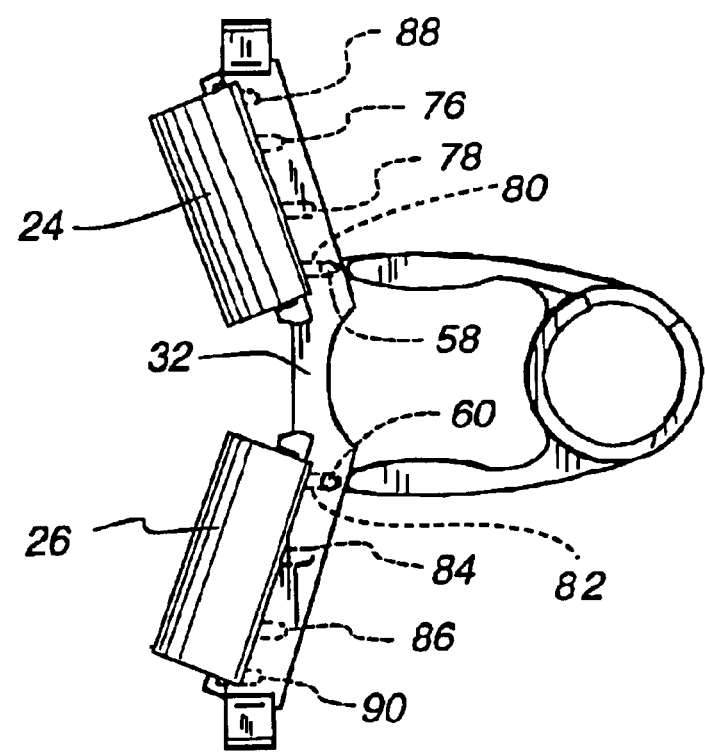
FIG. 8 is a top view of the forehead support of FIG. 1 in a fourth position.
Figure 9:
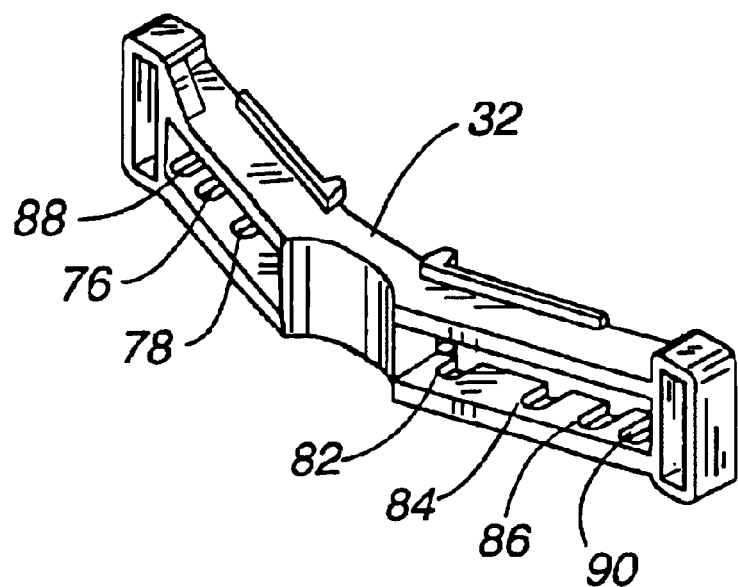
FIG. 9 is a front view of a bridge of the support of FIG. 1.
Figure 10:
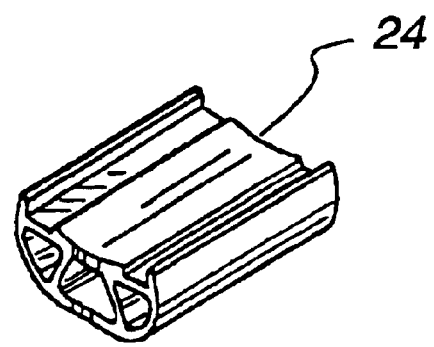
FIG. 10 is a single pad of the support of FIG. 1.
Figure 13:
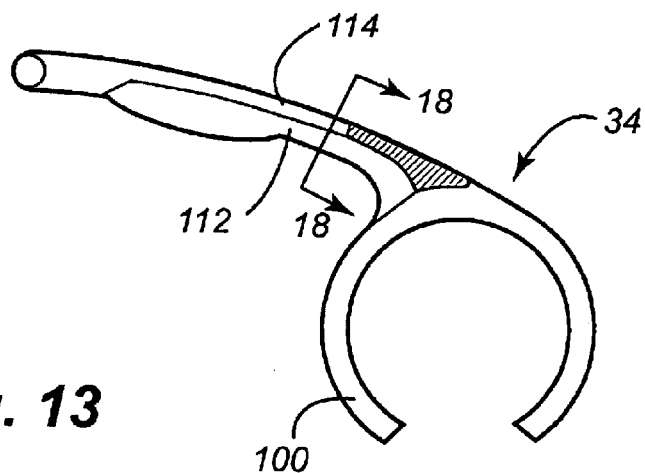
FIG. 13 is a section view of the arm of FIG. 12 along section line 13—13.
Figure 15:
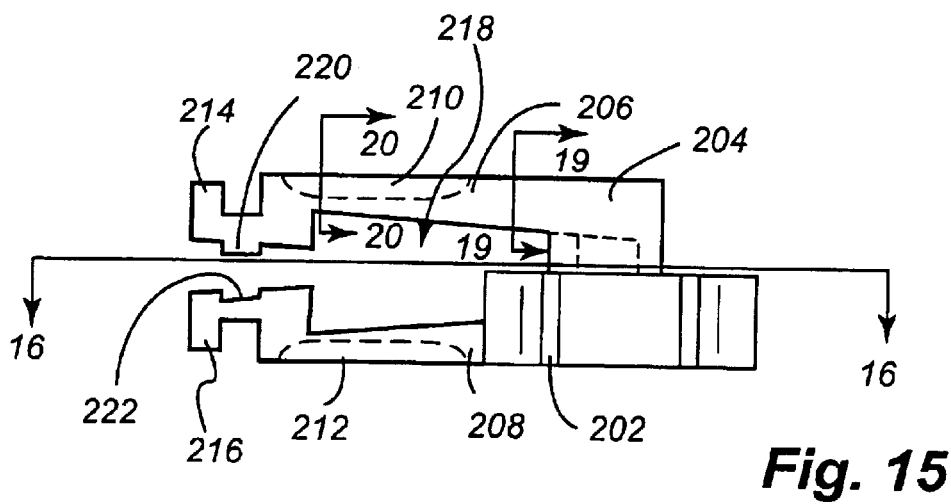
FIG. 15 is a side view of the arm of FIG. 14.
Figure 18:
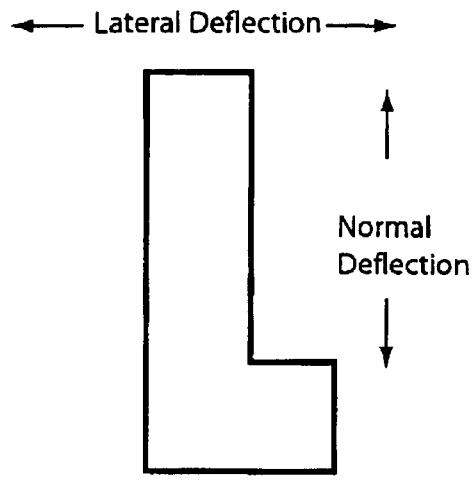
FIG. 18 is a partial section view of the arm of FIG. 13 along section line 18—18.

Even though the thickness of the cantilever arm portions of the arm of FIG. 15 have been reduced as compared to the arm of FIG. 2, the width of these portions has been increased with respect to the arm of FIG. 2. Compare the widths of the arm of FIG. 15 shown in FIGS. 19 and 20 with the width of the arm of FIG. 13 shown in FIG. 18. The increased width of the improved arm of FIG. 15 provides a stiffness in the lateral plane that is about 8 times greater than the stiffness of the arm of FIG. 2. This increased stiffness prevents most accidental lateral deflections of the pins and would likely require a determined intentional action to laterally deflect the cantilever arm portions and pins.

Figure 16:
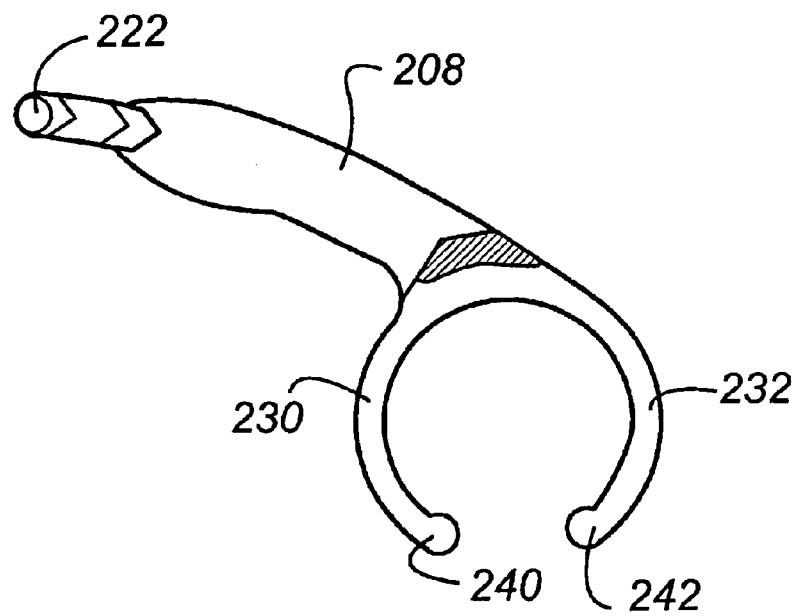
FIG. 16 is a section view of the arm of FIG. 15 along section line 16—16.
Figure 17:
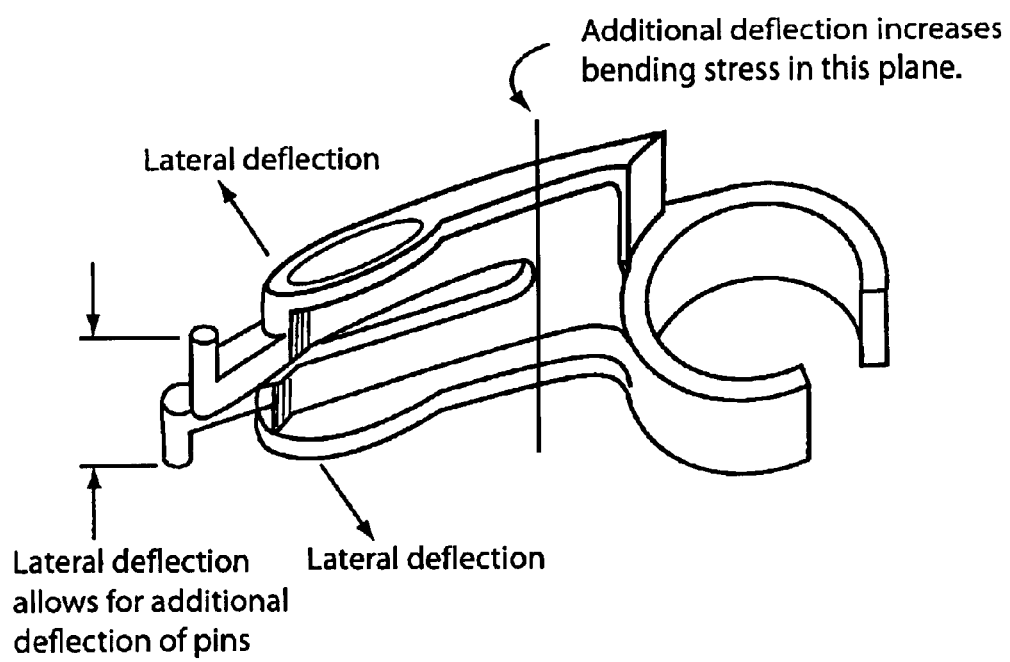
FIG. 17 is a perspective view of the arm of FIG. 11.

A male locking portion 220 is positioned inboard of pin 214 and a female locking portion 222 is correspondingly positioned inboard of pin 216. The male and female locking portions are configured so as to be able to fittingly mate with one another when the two flanges portions 206 and 208 are pressed together. As seen in FIG. 16, a section along line 16—16 in FIG. 15, the female locking portion can be configured as a chevron-shaped slot Correspondingly, the male locking portion 220 would be configured as a chevron-shaped projection to mate with the chevron-shaped slot of female locking portion 222. The male and female locking portions can also have different shapes, as long as they will lockingly mate together when the two flange portions are pressed together. As with the arm 34 above, the arm 200 can be flipped over to provide the second arm of the forehead support and thus, only one mold is needed to cast both required arms.

The lengths of the pins 214 and 216 are provided such that when the pins are pressed together to the extent allowed by the locking portions, the pins will clear the slots in the bridge, contrary to the pins of the related art arms.

In a preferred embodiment, these improved arms are constructed of a polycarbonate, specifically, Makrolon 2858 manufactured by Bayer.

Figure 11:
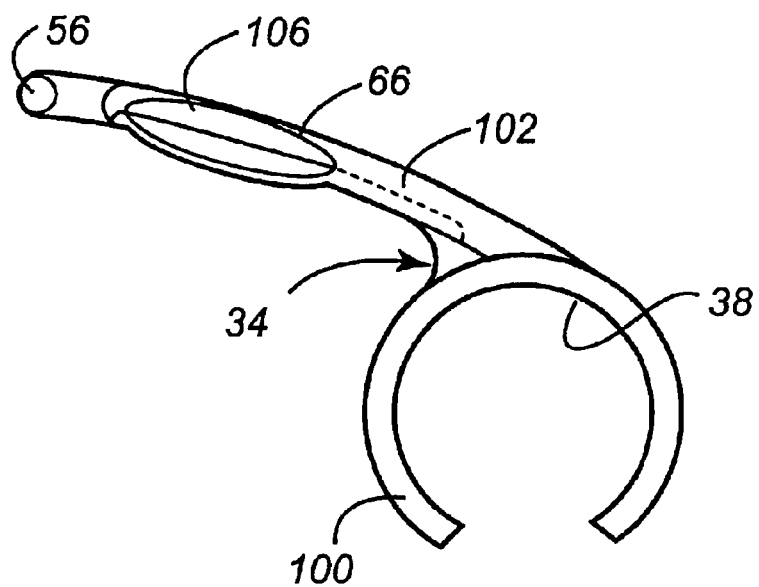
FIG. 11 is a top view of a of an arm for use in the forehead support of FIG. 2.

There are several advantages to this improved arm embodiment. First, because the space 218 extends farther along the arm 200, the lack of a web between the flanges 206 and 208 and the tapering of the cantilever arm portions, it is as easy or easier to press the pins 214 and 216 together when adjusting the forehead support, even with the increased lateral strength of the improved arms. This is especially important because during the adjustment while the mask is on the wearer's head, the wearer cannot easily see the forehead support as he or she is performing the adjustment. The increased lateral strength helps resist accidental lateral deflection of the cantilever arm portions and pins, as well as providing a stronger support to the airflow tube. The end result is that at the outer portion of the arm 200 near the pins, the extending portion 204 has a greater stiffness and resistance to bending in the lateral or horizontal direction (i.e., the pivoting direction) than it does in the vertical direction (the non-pivoting direction). This is contrary to the embodiment shown in FIGS. 11–13 where the stiffness and resistance to bending is greater in the vertical direction than in the horizontal direction.

Of course, the taper, shape and/or the thickness of the cantilevered arm portions can be altered to vary the stiffness of the cantilevered arm portions in the horizontal or vertical directions, as circumstances warrant. Further, under certain circumstances, it is contemplated that the stiffness of the cantilevered arm portions in the vertical direction can be less, similar to, or even greater than the comparable stiffness of the cantilevered arm portions of the related art design in the vertical direction.

The use of the wider flanges also allows the use of broader oval depressions 210 and 212. These broader depressions better accommodate the wearer's fingers and thus, give the wearer a more positive and more comfortable grip on the arms during adjustment.

The provision of the male and female locking portions assures that the two flange portions remained aligned with one another during the pressing together of the pins 214 and 216. Thus, the pins are also maintained in alignment during compression, making it easier for both pins to align with their respective slots in the bridge during adjustment of the bridge. Without the locking mechanism, the pins can be twisted and splayed with respect to another during compression, making it more difficult to position the pins in the desired respective slots in the bridge during adjustment. Further, the locking portions also prevent the user from laterally deflecting the pins with respect to one another when disassembling the arm from the bridge. Since the pins are short enough to clear the slots in the bridge when pressed together, the arm need not be rotated or the pins laterally displaced from one another to allow the pins to clear the slots in the bridge. This reduces that the chance that a user can operate the arms contrary to instructions and thereby place undue stresses on the arms that could lead to premature failure of the arms.

Finally, the provision of the undercut or recessed portions 236 and 238 on arc portions 230 and 232 reduces the amount of material of the arm that comes into contact with the airflow tube 12 (or other pivot point). This helps prevent sticking or binding of the arm as it is pivoted about the airflow tube during adjustment of the forehead support, as compared to the related arm embodiment. The radiused ends 240 and 242 are also less likely to catch and hang up on imperfections in the airflow tube during pivoting, as compared to the sharper ends of the related arm embodiment. Thus, the arm 200 more easily pivots about the airflow tube during adjustment of the forehead support.

These improvements in arm 200 thus make it easier to adjust the forehead support, as well as make it easier to disassemble the arms from the bridge to allow thorough cleaning of the bridge and other support components. They also help prevent actions by the user contrary to instructions that could increase the risk of breakage of the forehead support.

While several improvements have been discussed above, it is contemplated that an improved forehead support according to the present invention need not utilize all such improvements but can utilize one or more of such improvements in various combinations.

It is to be understood that while the invention has been described above in conjunction with preferred specific embodiments, the description and examples are intended to illustrate and not limit the scope of the invention.

What is claimed:

1. A forehead support constructed and arranged to be connected to and support a respiratory mask, comprising:
   a bridge constructed and arranged to engage a forehead of a user, the bridge having a first side and a second side, the bridge also having a plurality of first adjusting points spaced along the first side and a plurality of second adjusting points spaced along the second side;

a first arm having a bridge end and a mask end, the first arm bridge end having an engagement mechanism constructed and arranged for selectively engaging each of the plurality of first adjusting points, the first arm bridge end engagement mechanism comprising a pair of extending portions separated by a space, the extending portions constructed and arranged to be selectively movable relative to one another between an expanded position where the extending portions are separated by the space and a compressed position where the separating space is reduced, at least one of the extending portions having a stiffness greater in a horizontal direction than in a vertical direction; and a second arm having a bridge end and a mask end, the second arm bridge end having an engagement mechanism constructed and arranged for selectively engaging each of the plurality of second adjusting points, the second arm bridge end engagement mechanism comprising a pair of extending portions separated by a space, the extending portions constructed and arranged to be selectively movable relative to one another between an expanded position where the extending portions are separated by the space and a compressed position where the separating space is reduced, at least one of the extending portions having a stiffness greater in a horizontal direction than in a vertical direction;

wherein, selective movement of the first arm bridge engagement mechanism between the plurality of first adjusting points alters a spacing distance between the first side of the bridge and the first connecting portion and selective movement of the second arm bridge engagement mechanism between the plurality of second adjusting points alters a spacing distance between the second side of the bridge and the second connecting portion.

2. The forehead support of claim 1, wherein:

at least one of the first arm bridge end extending portions comprises a projecting pin; and each of the plurality of first adjusting points comprises a slot constructed and arranged for selective engagement with the first arm projecting pin when the first arm extending portions are in the expanded position, and for selective disengagement with the first arm projecting pin when the first arm extending portions are in the compressed position.

3. The forehead support of claim 2, wherein:

at least one of the second arm bridge end extending portions comprises a projecting pin; and each of the plurality of second adjusting points comprises a slot constructed and arranged for selective engagement with the second arm projecting pin when the second arm extending portions are in the expanded position, and for selective disengagement with the second arm projecting pin when the second arm extending portions are in the compressed position.

4. The forehead support of claim 3, wherein each of the plurality of first and second adjusting points comprises a pair of slots and each of the first and second arm extending portions comprises a projecting pin constructed and arranged for selective engagement and disengagement with one of the pair of slots, respectively.

5. The forehead support of claim 4, and further comprising the respiratory mask, the respiratory mask comprising an airflow tube, the first and second connecting portions being positioned on the airflow tube.

6. The forehead support of claim 5, wherein each of the first and second arm mask ends is pivotally connected about an axis of the airflow tube.

7. The forehead support of claim 6, and further comprising:

a first cushion pad connected to the first side of the bridge and constructed and arranged to be positioned between the bridge and the forehead of the user; and a second cushion pad connected to the second side of the bridge and constructed and arranged to be positioned between the bridge and the forehead of the user.

8. The forehead support of claim 7, wherein:

each of the first arm extending portions includes a locking portion constructed and arranged to mate with the other of the locking portions when the first arm extending portions are in the compressed position to thereby maintain alignment of the first arm extending portions in a direction of pivoting about the first connecting portion; and each of the second arm extending portions includes a locking portion constructed and arranged to mate with the other of the locking portions when the second extending portions are in the compressed position to thereby maintain alignment of the second arm extending portions in a direction of pivoting about the second connecting portion.

9. The forehead support of claim 8, wherein:

the first connecting portion is generally circular in shape, the first arm mask end has a portion that is generally circular constructed and arranged for pivotably connecting about the generally circular first connecting portion, and an internal surface of the generally circular portion of the first arm mask end includes at least one relieved portion to reduce an area of material contact between the first arm mask end and the first connecting portion; and the second connecting portion is generally circular in shape, the second arm mask end has a portion that is generally circular constructed and arranged for pivotably connecting about the generally circular second connecting portion, and an internal surface of the generally circular portion of the second arm mask end includes at least one relieved portion to reduce an area of material contact between the second arm mask end and the second connecting portion.

10. A forehead support constructed and arranged to be connected to and support a respiratory mask, comprising:

a bridge constructed and arranged to engage a forehead of a user, the bridge having a first side and a second side, the bridge also having a plurality of first adjusting points spaced along the first side and a plurality of second adjusting points spaced along the second side;

a first arm having a bridge end and a mask end, the first arm bridge end having an engagement mechanism constructed and arranged for selectively engaging each of the plurality of first adjusting points, the first arm bridge end engagement mechanism comprising a pair of extending portions separated by a space, the extending portions constructed and arranged to be selectively movable relative to one another between an expanded position where the extending portions are separated by the space and a compressed position where the separating space is reduced, each of the extending portions including a locking portion constructed and arranged to mate with the other of the locking portions when the extending portions are in the compressed position to thereby maintain alignment of the extending portions in a direction of pivoting about the first connecting portion; and a second arm having a bridge end and a mask end, the second arm bridge end having an engagement mechanism constructed and arranged for selectively engaging each of the plurality of second adjusting points, the second arm bridge end engagement mechanism comprising a pair of extending portions separated by a space, the extending portions constructed and arranged to be selectively movable relative to one another between an expanded position where the extending portions are separated by the space and a compressed position where the separating space is reduced, each of the extending portions including a locking portion constructed and arranged to mate with the other of the locking portions when the extending portions are in the compressed position to thereby maintain alignment of the extending portions in a direction of pivoting about the second connecting portion;

wherein, selective movement of the first arm bridge engagement mechanism between the plurality of first adjusting points alters a spacing distance between the first side of the bridge and the first connecting portion and selective movement of the second arm bridge engagement mechanism between the plurality of second adjusting points alters a spacing distance between the second side of the bridge and the second connecting portion.

11. The forehead support of claim 10, wherein:

at least one of the first arm bridge end extending portions comprises a projecting pin; and each of the plurality of first adjusting points comprises a slot constructed and arranged for selective engagement with the first arm projecting pin when the first arm extending portions are in the expanded position, and for selective disengagement with the first arm projecting pin when the first arm extending portions are in the compressed position.

12. The forehead support of claim 11, wherein:

at least one of the second arm bridge end extending portions comprises a projecting pin; and each of the plurality of second adjusting points comprises a slot constructed and arranged for selective engagement with the second arm projecting pin when the second arm extending portions are in the expanded position, and for selective disengagement with the second arm projecting pin when the second arm extending portions are in the compressed position.

13. The forehead support of claim 12, wherein each of the plurality of first and second adjusting points comprises a pair of slots and each of the first and second arm extending portions comprises a projecting pin constructed and arranged for selective engagement and disengagement with one of the pair of slots, respectively.

14. The forehead support of claim 13, and further comprising the respiratory mask, the respiratory mask comprising an airflow tube, the first and second connecting portions being positioned on the airflow tube.

15. The forehead support of claim 14, wherein each of the first and second arm mask ends is pivotally connected about an axis of the airflow tube.

16. The forehead support of claim 15, and further comprising:

a first cushion pad connected to the first side of the bridge and constructed and arranged to be positioned between the bridge and the forehead of the user; and a second cushion pad connected to the second side of the bridge and constructed and arranged to be positioned between the bridge and the forehead of the user.

17. The forehead support of claim 16, wherein:

the first connecting portion is generally circular in shape, the first arm mask end has a portion that is generally circular constructed and arranged for pivotably connecting about the generally circular first connecting portion, and an internal surface of the generally circular portion of the first arm mask end includes at least one relieved portion to reduce an area of material contact between the first arm mask end and the first connecting portion; and the second connecting portion is generally circular in shape, the second arm mask end has a portion that is generally circular constructed and arranged for pivotably connecting about the generally circular second connecting portion, and an internal surface of the generally circular portion of the second arm mask end includes at least one relieved portion to reduce an area of material contact between the second arm mask end and the second connecting portion.

18. A forehead support constructed and arranged to be connected to and support a respiratory mask, comprising:

a bridge constructed and arranged to engage a forehead of a user, the bridge having a first side and a second side, the bridge also having a plurality of first adjusting points spaced along the first side and a plurality of second adjusting points spaced along the second side;

a first arm having a bridge end and a mask end, the first arm bridge end having an engagement mechanism constructed and arranged for selectively engaging each of the plurality of first adjusting points; and a second arm having a bridge end and a mask end, the second arm bridge end having an engagement mechanism constructed and arranged for selectively engaging each of the plurality of second adjusting points;

wherein:

selective movement of the first arm bridge engagement mechanism between the plurality of first adjusting points alters a spacing distance between the first side of the bridge and the first connecting portion, selective movement of the second arm bridge engagement mechanism between the plurality of second adjusting points alters a spacing distance between the second side of the bridge and the second connecting portion, and the mask end includes a semi-circular portion having at least one arc portion with an undercut.

19. The forehead support of claim 18, wherein:

the first arm bridge end engagement mechanism comprises a pair of extending portions separated by a space, the extending portions constructed and arranged to be selectively movable relative to one another between an expanded position where the extending portions are separated by the space and a compressed position where the separating space is reduced; and the second arm bridge end engagement mechanism comprises a pair of extending portions separated by a space, the extending portions constructed and arranged to be selectively movable relative to one another between an expanded position where the extending portions are separated by the space and a compressed position where the separating space is reduced.

20. The forehead support of claim 19, wherein:

at least one of the first arm bridge end extending portions comprises a projecting pin; and each of the plurality of first adjusting points comprises a slot constructed and arranged for selective engagement with the first arm projecting pin when the first arm extending portions are in the expanded position, and for selective disengagement with the first arm projecting pin when the first arm extending portions are in the compressed position.

21. A forehead support constructed and arranged to be connected to and support a respiratory mask, comprising:

a bridge constructed and arranged to engage a forehead of a user, the bridge having a first side and a second side, the bridge also having a plurality of first adjusting points spaced along the first side and a plurality of second adjusting points spaced along the second side;

a first arm having a bridge end and a mask end, the first arm bridge end having an engagement mechanism constructed and arranged for selectively engaging each of the plurality of first adjusting points; and a second arm having a bridge end and a mask end, the second arm bridge end having an engagement mechanism constructed and arranged for selectively engaging each of the plurality of second adjusting points, wherein each of the first and second arms includes an extending portion defining upper and lower flange portions each having a proximal end, a distal end and a central portion, wherein a width of the flange portion along the proximal and central portions is substantially wider than a width of the distal end.

22. The forehead support according to claim 21, wherein each of the upper and lower flange portions includes a generally oval depression.

23. A forehead support constructed and arranged to be connected to and support a respiratory mask, comprising:

a bridge constructed and arranged to engage a forehead of a user, the bridge having a first side and a second side, the bridge also having a plurality of first adjusting points spaced along the first side and a plurality of second adjusting points spaced along the second side;

a first arm having a bridge end and a mask end, the first arm bridge end having an engagement mechanism constructed and arranged for selectively engaging each of the plurality of first adjusting points; and a second arm having a bridge end and a mask end, the second arm bridge end having an engagement mechanism constructed and arranged for selectively engaging each of the plurality of second adjusting points, wherein:

each of the first and second arms define upper and lower flange portions, each of the upper and lower flange portions includes a distal end including a bridge engagement pin, the upper and lower flange portions are positioned to be opposed to one another and are resiliently flexible into a common space upon compression of the upper flange portion, and the upper flange portion includes an upper mating portion inboard of the engagement pin of the upper flange and the lower flange portion includes a lower mating portion inboard of the engagement pin of the lower flange portion, whereby the upper and lower mating portions mate upon full compression of the flange portions, and separate upon release of the arm portions.

24. The forehead support according to claim 23, wherein the upper and lower flange portions include a male and female mating assembly.

25. The forehead support according to claim 24, wherein the mating assembly includes a chevron-shaped slot and a chevron-shaped projection.

26. A forehead support constructed and arranged to be connected to and support a respiratory mask, comprising:

a bridge constructed and arranged to engage a forehead of a user, the bridge having a first side and a second side, the bridge also having a plurality of first adjusting points spaced along the first side and a plurality of second adjusting points spaced along the second side;

a first arm having a bridge end and a mask end, the first arm bridge end having an engagement mechanism constructed and arranged for selectively engaging each of the plurality of first adjusting points; and a second arm having a bridge end and a mask end, the second arm bridge end having an engagement mechanism constructed and arranged for selectively engaging each of the plurality of second adjusting points, wherein each of the first and second arms defines upper and lower arm portions, wherein each of the upper and lower arm portions is tapered down from a proximal end to a distal end thereof.

27. The forehead support according to claim 26, wherein a space is provided between the upper and lower arm portions, the space having a generally trapezoidal shape.

28. A forehead support constructed and arranged to be connected to and support a respiratory mask, comprising:

a bridge constructed and arranged to engage a forehead of a user, the bridge having a first side and a second side, the bridge also having a plurality of first adjusting points spaced along the first side and a plurality of second adjusting points spaced along the second side;

a first arm having a bridge end and a mask end, the first arm bridge end having an engagement mechanism constructed and arranged for selectively engaging each of the plurality of first adjusting points; and a second arm having a bridge end and a mask end, the second arm bridge end having an engagement mechanism constructed and arranged for selectively engaging each of the plurality of second adjusting points, wherein:

each of the first and second arms includes an extending portion defining upper and lower arm portions, and near a distal end portions of each of the upper and lower arm portions, the extending portion has a greater stiffness and resistance in the lateral direction than in a direction transverse to the lateral direction.

* * * * *